United States Patent
Kono et al.

(10) Patent No.: US 12,021,191 B2
(45) Date of Patent: Jun. 25, 2024

(54) ADDITIVE FOR NONAQUEOUS ELECTROLYTE SOLUTIONS, NONAQUEOUS ELECTROLYTE SOLUTION AND ELECTRICITY STORAGE DEVICE

(71) Applicant: SUMITOMO SEIKA CHEMICALS CO., LTD., Hyogo (JP)

(72) Inventors: Yuki Kono, Hyogo (JP); Yasuyuki Takai, Hyogo (JP); Noriko Yamamoto, Hyogo (JP); Koji Fujita, Hyogo (JP)

(73) Assignee: SUMITOMO SEIKA CHEMICALS CO., LTD., Hyogo (JP)

( * ) Notice: Subject to any disclaimer, the term of this patent is extended or adjusted under 35 U.S.C. 154(b) by 154 days.

(21) Appl. No.: 16/760,336

(22) PCT Filed: Oct. 30, 2018

(86) PCT No.: PCT/JP2018/040397
§ 371 (c)(1),
(2) Date: Apr. 29, 2020

(87) PCT Pub. No.: WO2019/088127
PCT Pub. Date: May 9, 2019

(65) Prior Publication Data
US 2021/0184259 A1    Jun. 17, 2021

(30) Foreign Application Priority Data
Oct. 31, 2017    (JP) .................... 2017-210779

(51) Int. Cl.
*H01M 10/0567*    (2010.01)
*C07D 333/48*    (2006.01)
(Continued)

(52) U.S. Cl.
CPC ...... *H01M 10/0567* (2013.01); *C07D 333/48* (2013.01); *H01G 11/60* (2013.01);
(Continued)

(58) Field of Classification Search
CPC ............... H01M 10/05; H01M 10/056; H01M 10/0569; H01M 10/0567; H01M 10/052; H01M 10/4235; H01G 11/64
See application file for complete search history.

(56) References Cited

U.S. PATENT DOCUMENTS

| | | | |
|---|---|---|---|
| 4,069,112 A | 1/1978 | Harbulak | |
| 2017/0271715 A1 | 9/2017 | Kim et al. | |
| 2018/0248226 A1* | 8/2018 | Kono | .................. H01M 10/052 |

FOREIGN PATENT DOCUMENTS

| | | |
|---|---|---|
| BE | 855425 | 10/1977 |
| CN | 103493280 | 1/2014 |

(Continued)

OTHER PUBLICATIONS

The extended European search report issued for European patent application No. 18873931.2, Jul. 12, 2021, 10 pages.
(Continued)

*Primary Examiner* — Matthew T Martin
*Assistant Examiner* — Ankith R Sripathi
(74) *Attorney, Agent, or Firm* — HSML P.C.

(57) ABSTRACT

Disclosed is an additive for a nonaqueous electrolyte solution, including a compound represented by the following formula (1):

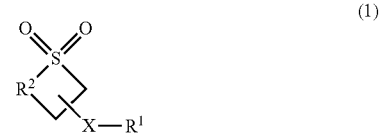

(1)

in formula (1), X represents a sulfonyl group or a carbonyl group, $R^1$ represents an alkyl group having 1 to 4
(Continued)

carbon atoms, which may be substituted with a halogen atom, a hydroxyl group, or the like, and $R^2$ represents a hydrocarbon group having 1 to 3 carbon atoms, which may be substituted with a halogen atom.

13 Claims, 1 Drawing Sheet

(51) Int. Cl.
    *H01G 11/60*     (2013.01)
    *H01G 11/62*     (2013.01)
    *H01G 11/64*     (2013.01)
    *H01M 10/0525*     (2010.01)
    *H01M 10/0568*     (2010.01)
    *H01M 10/0569*     (2010.01)

(52) U.S. Cl.
    CPC .............. *H01G 11/62* (2013.01); *H01G 11/64* (2013.01); *H01M 10/0525* (2013.01); *H01M 10/0568* (2013.01); *H01M 10/0569* (2013.01); *H01M 2300/0037* (2013.01)

(56) References Cited

FOREIGN PATENT DOCUMENTS

| | | |
|---|---|---|
| CN | 103947030 | 7/2014 |
| CN | 104067361 | 9/2014 |
| EP | 2755272 | 7/2014 |
| EP | 2833381 | 2/2015 |
| GB | 1024644 | 3/1966 |
| GB | 1090308 | 11/1967 |
| JP | S63-102173 | 5/1988 |
| JP | H5-074486 | 3/1993 |
| JP | H10-050342 | 2/1998 |
| JP | 2012-056925 | 3/2012 |
| KR | 10-2017-0108589 | 9/2017 |
| TW | 201714338 | 4/2017 |
| WO | 2012/147818 | 11/2012 |
| WO | 2017/043576 | 3/2017 |

OTHER PUBLICATIONS

International Preliminary Report on Patentability of PCT/JP2018/040397, May 14, 2020, 7 pages.

* cited by examiner

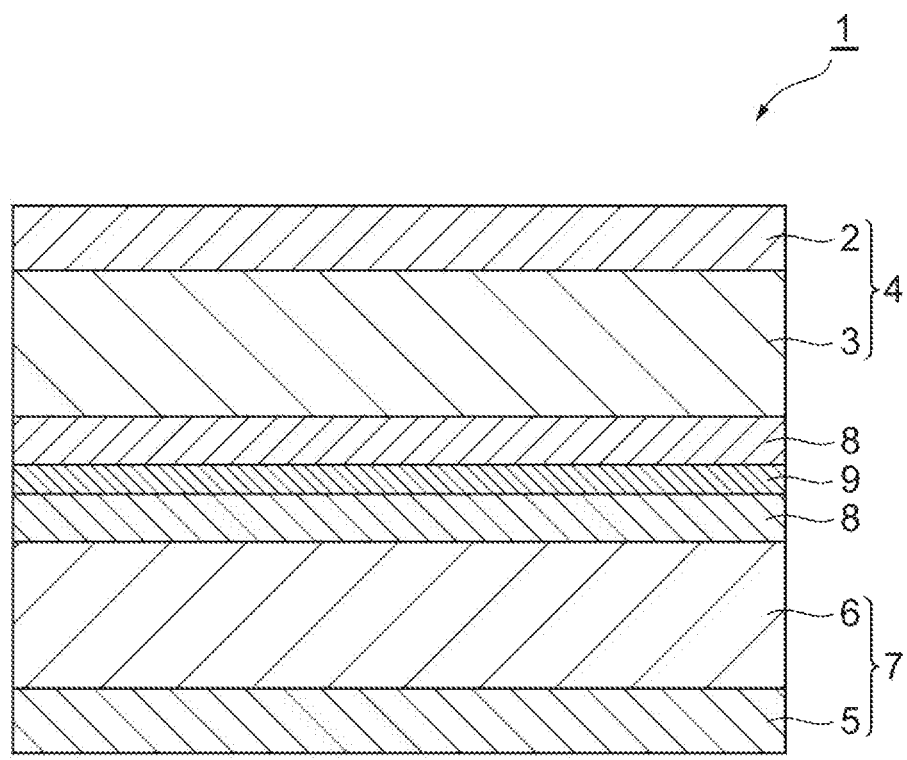

ADDITIVE FOR NONAQUEOUS ELECTROLYTE SOLUTIONS, NONAQUEOUS ELECTROLYTE SOLUTION AND ELECTRICITY STORAGE DEVICE

TECHNICAL FIELD

The present invention relates to an additive for a nonaqueous electrolyte solution. Furthermore, the present invention also relates to a nonaqueous electrolyte solution using the additive for a nonaqueous electrolyte solution, and an electricity storage device using the nonaqueous electrolyte solution.

BACKGROUND ART

In recent years, along with an increase in attention to solving environmental problems and establishing a sustainable recycling-based society, nonaqueous electrolyte solution secondary batteries typified by lithium ion batteries and electricity storage devices such as electric double layer capacitors have been extensively studied. Among those, the lithium ion batteries have been used as power supplies for laptops, mobile phones, and the like from the viewpoint that they have high working voltages and energy densities. These lithium ion batteries are promising as a new power supply from the viewpoint that they have high energy densities, as compared with lead batteries and nickel-cadmium batteries, and can establish a higher capacity.

The lithium ion batteries have a problem in that a battery capacity is decreased over charge and discharge cycles. As a method for suppressing such the decrease in a battery capacity over charge and discharge cycles, a method of adding various additives to an electrolyte solution has been examined. The additives decompose during an initial charge and discharge to form a film called a solid electrolyte interface (SEI) on the surface of an electrode. Since the SEI is formed during the initial charge and discharge cycle, electricity is consumed for decomposition of a solvent in the electrolyte solution in no case, and the lithium ions can transfer between the electrodes through the SEI. That is, formation of the SEI contributes to suppression of deterioration of an electricity storage device such as a nonaqueous electrolyte solution secondary battery in a case of repeating charge and discharge cycles, and to improvement of battery characteristics, storage characteristics, load characteristics, and the like.

With regard to a compound that forms an SEI, for example, Patent Document 1 discloses that the charge and discharge cycle characteristics of a lithium secondary battery are improved by adding 1,3-propanesultone (PS) as an additive into an electrolyte solution. Patent Document 2 discloses that the self-discharge rate of a nonaqueous electrolyte secondary battery is reduced by adding 1,3,2-dioxaphosphoran-2-dioxide derivative or PS as additives into an electrolyte solution. Patent Document 3 discloses that the discharge characteristics and the like of a lithium secondary battery are improved by adding a derivative of vinylene carbonate (VC) as an additive into an electrolyte solution.

CITATION LIST

Patent Literature

[Patent Document 1] Japanese Unexamined Patent Publication No. S63-102173

[Patent Document 2] Japanese Unexamined Patent Publication No. H10-050342

[Patent Document 3] Japanese Unexamined Patent Publication No. H05-074486

SUMMARY OF INVENTION

Technical Problem

However, sufficient performance cannot be obtained in some cases even with a use of these additives. Therefore, there is a demand for development of a new additive which further improves the battery characteristics of an electricity storage device.

An object of the present invention is to provide an additive for a nonaqueous electrolyte solution, which is capable of suppressing generation of a gas from a nonaqueous electrolyte solution, in addition to improving charge characteristics and resistance characteristics, in a case where the additive for a nonaqueous electrolyte solution is used in an electricity storage device such as a nonaqueous electrolyte solution secondary battery. Further, another object of the present invention is to provide a nonaqueous electrolyte solution using the additive for a nonaqueous electrolyte solution and an electricity storage device using the nonaqueous electrolyte solution.

Solution to Problem

The present invention provides an additive for a nonaqueous electrolyte solution, including a compound represented by the following formula (1).

In formula (1), X represents a sulfonyl group or a carbonyl group, $R^1$ represents an alkyl group having 1 to 4 carbon atoms, which may be substituted with a halogen atom, an alkenyl group having 2 to 4 carbon atoms, which may be substituted with a halogen atom, an alkynyl group having 2 to 4 carbon atoms, which may be substituted with a halogen atom, an aryl group which may be substituted with a halogen atom, an alkoxy group having 1 to 4 carbon atoms, which may be substituted with a halogen atom, an alkenyloxy group having 2 to 4 carbon atoms, which may be substituted with a halogen atom, an alkynyloxy group having 2 to 4 carbon atoms, which may be substituted with a halogen atom, an aryloxy group which may be substituted with a halogen atom, a hydroxyl group, or a lithium oxy group. $R^2$ represents a hydrocarbon group having 1 to 3 carbon atoms, which may be substituted with a halogen atom. In the present specification, an expression, "(which) may be substituted with a halogen atom" means that a hydrogen atom included in each group may be substituted with a halogen atom.

Advantageous Effects of Invention

According to the present invention, it is possible to provide an additive for a nonaqueous electrolyte solution, which is capable of suppressing generation of a gas from a nonaqueous electrolyte solution, in addition to improving charge characteristics and resistance characteristics, in a case where the additive for a nonaqueous electrolyte solution is used in an electricity storage device such as a nonaqueous electrolyte solution secondary battery. The present invention also provides a nonaqueous electrolyte solution using the additive for a nonaqueous electrolyte solution and an electricity storage device using the nonaqueous electrolyte solution.

BRIEF DESCRIPTION OF DRAWINGS

FIG. 1 is a cross-sectional view schematically showing an example of a nonaqueous electrolyte solution secondary battery.

DESCRIPTION OF EMBODIMENTS

An additive for a nonaqueous electrolyte solution according to one embodiment includes a compound represented by the following formula (1).

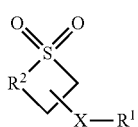
(1)

In formula (1), X represents a sulfonyl group or a carbonyl group, $R^1$ represents an alkyl group having 1 to 4 carbon atoms, which may be substituted with a halogen atom, an alkenyl group having 2 to 4 carbon atoms, which may be substituted with a halogen atom, an alkynyl group having 2 to 4 carbon atoms, which may be substituted with a halogen atom, an aryl group which may be substituted with a halogen atom, an alkoxy group having 1 to 4 carbon atoms, which may be substituted with a halogen atom, an alkenyloxy group having 2 to 4 carbon atoms, which may be substituted with a halogen atom, an alkynyloxy group having 2 to 4 carbon atoms, which may be substituted with a halogen atom, an aryloxy group which may be substituted with a halogen atom, a hydroxyl group, or a lithium oxy group. $R^2$ represents a hydrocarbon group having 1 to 3 carbon atoms, which may be substituted with a halogen atom.

The compound represented by formula (1) is a cyclic sulfone compound. It is considered that the cyclic sulfone compound forms a rigid SEI by causing ring-opening polymerization.

The compound represented by formula (1) may be a compound represented by the following formula (2) from the viewpoint of further improving cycle characteristics.

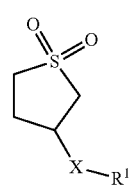
(2)

In formula (2), X and $R^1$ have the same definitions as X and $R^1$, respectively, in formula (1).

In formula (1) and formula (2), X may be a sulfonyl group from the viewpoints that battery resistance is likely to be lowered and gas generation is likely to be suppressed.

In a case where the group represented by $R^1$ is an alkyl group having 1 to 4 carbon atoms, which may be substituted with a halogen atom, examples of the alkyl group include a methyl group, an ethyl group, an n-propyl group, an isopropyl group, an n-butyl group, an isobutyl group, a t-butyl group, and a trifluoromethyl group. Among those, from the viewpoint that the battery resistance is further lowered, the group represented by $R^1$ may be the methyl group, the ethyl group, or the t-butyl group, or may also be the methyl group.

In a case where the group represented by $R^1$ is an alkenyl group having 2 to 4 carbon atoms, which may be substituted with a halogen atom, examples of the alkenyl group include a vinyl group, an allyl group, an isopropenyl group, a 1-butenyl group, a 2-butenyl group, a 3-butenyl group, an isobutenyl group, and a 1,1-difluoro-1-propenyl group. Among those, the group represented by $R^1$ may be the allyl group.

In a case where the group represented by $R^1$ is an alkynyl group having 2 to 4 carbon atoms, which may be substituted with a halogen atom, examples of the alkynyl group include a 1-propynyl group, a 2-propynyl group, a 1-butynyl group, a 2-butynyl group, and a 3-butynyl group. Among those, the group represented by $R^1$ may be the 2-propynyl group.

In a case where the group represented by $R^1$ is an aryl group which may be substituted with a halogen atom, examples of the aryl group include a phenyl group, a tosyl group, a xylyl group, and a naphthyl group.

In a case where the group represented by $R^1$ is an alkoxy group having 1 to 4 carbon atoms, which may be substituted with a halogen atom, examples of the alkoxy group include a methoxy group, an ethoxy group, an n-propoxy group, and an n-butoxy group.

In a case where the group represented by $R^1$ is an alkenyloxy group having 2 to 4 carbon atoms, which may be substituted with a halogen atom, examples of the alkenyloxy group include a 2-propenyloxy group, a 1-methyl-2-propenyloxy group, a 2-methyl-2-propenyloxy group, a 2-butenyloxy group, and a 3-butenyloxy group.

In a case where the group represented by $R^1$ is an alkynyloxy group having 2 to 4 carbon atoms, which may be substituted with a halogen atom, examples of the alkynyloxy group include a 2-propynyloxy group, a 1-methyl-2-propynyloxy group, a 2-methyl-2-propynyl group, a 2-butynyloxy group, and a 3-butynyloxy group.

In a case where the group represented by $R^1$ is an aryloxy group which may be substituted with a halogen atom, examples of the aryloxy group include a phenoxy group, a 2-methylphenoxy group, a 3-methylphenoxy group, a 4-methylphenoxy group, a 2-ethylphenoxy group, a 3-ethylphenoxy group, a 4-ethylphenoxy group, a 2-methoxyphenoxy group, a 3-methoxyphenoxy group, and a 4-methoxyphenoxy group.

In a case where the group represented by $R^1$ is substituted with a halogen atom, examples of the halogen atom include an iodine atom, a bromine atom, and a fluorine atom. Among those, from the viewpoint that the battery resistance is likely to be further lowered, the group represented by $R^1$ may be substituted with the fluorine atom.

In formulae (1) and (2), from the viewpoint that the battery resistance is likely to be lowered, $R^1$ may be an alkyl group having 1 to 4 carbon atoms, which may be substituted with a halogen atom, an alkenyl group having 2 to 4 carbon atoms, which may be substituted with a halogen atom, an alkynyl group having 2 to 4 carbon atoms, which may be substituted with a halogen atom, an aryl group which may be substituted with a halogen atom, an alkoxy group having 1 to 4 carbon atoms, which may be substituted with a halogen atom, an alkenyloxy group having 2 to 4 carbon atoms, which may be substituted with a halogen atom, an alkynyloxy group having 2 to 4 carbon atoms, which may be substituted with a halogen atom, or an aryloxy group which may be substituted with a halogen atom.

The group represented by $R^2$ represents a hydrocarbon group having 1 to 3 carbon atoms, which may be substituted with a halogen atom. Specific examples of the group represented by $R^2$ include —$CH_2$—, —$CH_2CH_2$—, —$CH_2CH_2CH_2$—, —$CFHCH_2$—, and —$CF_2CH_2$—. Among those, from the viewpoint that the battery resistance is likely to be lowered, the group represented by $R^2$ may be a hydrocarbon group having 2 carbon atoms, which may be substituted with a halogen atom, or —$CH_2CH_2$—.

Examples of the compound represented by formula (1) include 3-methanesulfonyl tetrahydrothiophene-1,1-dioxide, 3-ethanesulfonyl tetrahydrothiophene-1,1-dioxide, 3-propanesulfonyl tetrahydrothiophene-1,1-dioxide, 3-tert-butylsulfonyl tetrahydrothiophene-1,1-dioxide, 3-phenylsulfonyl tetrahydrothiophene-1,1-dioxide, 3-trifluoromethanesulfonyl tetrahydrothiophene-1,1-dioxide, 3-thiophenesulfonic acid tetrahydroxy-1,1-dioxide, lithium 3-thiophene sulfonate, 3-methoxysulfonyl tetrahydrothiophene-1,1-dioxide, 3-acetyltetrahydrothiophene-1,1-dioxide, and 3-methanesulfonyl tetrahydrothiopyran-1,1-dioxide. From the viewpoint of the resistance of the formed SEI film, the compound represented by formula (1) may be at least one compound selected from the group consisting of 3-methanesulfonyl tetrahydrothiophene-1,1-dioxide, 3-ethanesulfonyl tetrahydrothiophene-1,1-dioxide, 3-propanesulfonyl tetrahydrothiophene-1,1-dioxide, 3-tert-butylsulfonyl tetrahydrothiophene-1,1-dioxide, 3-thiophenesulfonic acid tetrahydroxy-1,1-dioxide, and 3-acetyltetrahydrothiophene-1,1-dioxide, and may also be 3-methanesulfonyl tetrahydrothiophene-1,1-dioxide, 3-ethanesulfonyl tetrahydrothiophene-1,1-dioxide, or a combination thereof.

The compound represented by formula (1) may be synthesized by combination of ordinary reactions using available raw materials. For example, in a case of synthesizing the compound in which X is a sulfonyl group, the compound can be synthesized by reacting 3-sulfolene having $R^1$ with a corresponding thiol compound (or a sodium salt of the thiol compound) to oxidize a reaction product.

A nonaqueous electrolyte solution is prepared by adding an additive for a nonaqueous electrolyte solution including the compound represented by formula (1) to a nonaqueous solvent in which an electrolyte is dissolved.

The additive for a nonaqueous electrolyte solution according to one embodiment may include at least one compound represented by formula (1) singly or may include two or more compounds compound represented by formula (1).

The additive for a nonaqueous electrolyte solution according to the present embodiment may include a compound which can contribute to formation of an SEI and/or other general components, in addition to the compound of formula (1), within a range that does not significantly interfere with the effects exerted by the present invention. Alternatively, only the compound of formula (1) may be used as the additive for a nonaqueous electrolyte solution. Examples of such other general components include vinylene carbonate (VC), fluoroethylene carbonate (FEC), 1,3-propane sultone (PS), a methylene methane disulfonate, a negative electrode protecting agent, a positive electrode protecting agent, a flame retardant, and an anti-overcharging agent.

The content of the additive in the nonaqueous electrolyte solution may be 0.005% to 10% by mass with respect to the total mass of the nonaqueous electrolyte solution. In a case where the content of the additive is 0.005% by mass or more, a stable SEI is likely to be sufficiently formed by an electrochemical reaction on the surface of the electrode, and therefore, it is possible to obtain more excellent battery characteristics. In a case where the content of the additive is 10% by mass or less, it is difficult for the viscosity of the nonaqueous electrolyte solution to increase, and therefore, it is possible to sufficiently secure the mobility of the ions. The content of the compound represented by formula (1) may be 0.005% to 10% by mass with respect to the total mass of the nonaqueous electrolyte solution.

From the same viewpoint, the content of the additive (or the compound represented by formula (1)) may be 0.01% by mass or more, 0.1% by mass or more, or 0.5% by mass or more, with respect to the total mass of the nonaqueous electrolyte solution. From the same viewpoint, the content of the additive (or the compound represented by formula (1)) may be 5% by mass or less or 2.0% by mass or less. In a case where the nonaqueous electrolyte solution includes two or more compounds represented by formula (1), a total amount thereof is regarded as a content of the additive (or the compound represented by formula (1)).

From the viewpoints of, for example, suppressing the viscosity of the obtained nonaqueous electrolyte solution to a lower value, the nonaqueous solvent may be an aprotic solvent. The nonaqueous solvent may be at least one selected from the group consisting of a cyclic carbonate, a chained carbonate, an aliphatic carboxylic acid ester, a lactone, a lactam, a cyclic ether, a chained ether, a sulfone, a nitrile, and halogen derivatives thereof. The nonaqueous solvent may be the cyclic carbonate or the chained carbonate, or may be a combination of the cyclic carbonate and the chained carbonate.

Examples of the cyclic carbonate include ethylene carbonate, propylene carbonate, and butylene carbonate. Examples of the chained carbonate include dimethyl carbonate, diethyl carbonate, and ethyl methyl carbonate. Examples of the aliphatic carboxylic acid ester include methyl acetate, ethyl acetate, methyl propionate, ethyl propionate, methyl butyrate, methyl isobutyrate, and methyl trimethylacetate. Examples of the lactone include γ-butyrolactone.

Examples of the lactam include ε-caprolactam and N-methylpyrrolidone. Examples of the cyclic ether include tetrahydrofuran, 2-methyltetrahydrofuran, tetrahydropyran, and 1,3-dioxolane. Examples of the chained ether include 1,2-diethoxyethane and ethoxymethoxyethane. Examples of the sulfone include sulfolane. Examples of the nitrile include acetonitrile. Examples of the halogen derivative include 4-fluoro-1,3-dioxolan-2-one, 4-chloro-1,3-dioxolan-2-one, and 4,5-difluoro-1,3-dioxolan-2-one. These nonaqueous solvents may be used singly or in combination of two or more kinds thereof. These nonaqueous solvents are particularly suitable in applications of, for example, a nonaqueous electrolyte solution secondary battery such as a lithium ion battery and an electric double layer capacitor such as a lithium ion capacitor.

The electrolyte may be a lithium salt serving as an ion source of lithium ions. The electrolyte may include at least one selected from the group consisting of $LiAlCl_4$, $LiBF_4$, $LiPF_6$, $LiClO_4$, $LiAsF_6$, and $LiSbF_6$. It is possible to increase a degree of dissociation or increase the ionic conductivity of the electrolyte solution, and further from the viewpoints that, for example, such the electrolyte has a function to suppress performance deterioration of an electric storage device caused by a long-term use due to oxidation reduction characteristics, the electrolyte may be $LiBF_4$ or $LiPF_6$. These electrolytes may be used singly or in combination of two or more kinds thereof.

In a case where the electrolyte includes $LiBF_4$ and $LiPF_6$, the nonaqueous solvent may include a combination of one or more of the cyclic carbonates and a combination of one or more of the chained carbonates. In particular, the electrolyte may include $LiBF_4$ and/or $LiPF_6$ and the nonaqueous solvent may include a combination of ethylene carbonate and diethyl carbonate.

The concentration of the electrolyte in the nonaqueous electrolyte solution of the present embodiment may be in the range of 0.1 to 2.0 mol/L with respect to the volume of the nonaqueous solvent. In a case where the concentration of the electrolyte is 0.1 mol/L or more, more excellent discharge characteristics or charge characteristics, and the like are obtained. In a case where the concentration of the electrolyte is 2.0 mol/L or less, it is difficult for the viscosity of the nonaqueous electrolyte solution to increase, and therefore, the ion mobility can be sufficiently secured. From the same viewpoint, the concentration of the electrolyte may be in the range of 0.5 to 1.5 mol/L.

The nonaqueous electrolyte solution of the present embodiment can be used as, for example, an electrolyte solution of an electricity storage device comprising a positive electrode and a negative electrode. More specifically, in a case where a nonaqueous electrolyte solution prepared using the additive for a nonaqueous electrolyte solution according to the present embodiment is used in an electricity storage device, such as a nonaqueous electrolyte solution secondary battery such as a lithium ion battery and an electric double layer capacitor such as a lithium ion capacitor, the charge characteristics and the resistance characteristics can be improved. In addition, the additive for a nonaqueous electrolyte solution according to the present embodiment can also suppress the generation of a gas such as carbon dioxide due to decomposition of the electrolyte solution accompanying charge and discharge, thereby improving battery performance and safety.

FIG. 1 is a cross-sectional view schematically showing one example of a nonaqueous electrolyte solution secondary battery which is an electricity storage device. A nonaqueous electrolyte solution secondary battery 1 shown in FIG. 1 has a positive electrode plate 4 and a negative electrode plate 7. The positive electrode plate 4 is constituted with a positive electrode collector 2 and a positive electrode active material layer 3 provided on the inner surface side of the positive electrode collector 2. The negative electrode plate 7 is constituted with a negative electrode collector 5 and a negative electrode active material layer 6 provided on the inner surface side of the negative electrode collector 5. The positive electrode plate 4 and the negative electrode plate 7 are arranged to face each other via a nonaqueous electrolyte solution 8. A separator 9 is arranged in the nonaqueous electrolyte solution 8.

As the positive electrode collector 2 and the negative electrode collector 5, for example, a metal foil formed of a metal such as aluminum, copper, nickel, and stainless steel can be used.

The positive electrode active material layer 3 of the positive electrode mainly includes a positive electrode active material. The positive electrode active material may be a lithium-containing composite oxide. The positive electrode active material may include at least one lithium-containing composite oxide selected from the group consisting of $LiMnO_2$, $LiFeO_2$, $LiCoO_2$, $LiMn_2O_4$, $Li_2FeSiO_4$, $Li(Ni_xCo_yM_z)O_2$ (x, y, and z are numerical values satisfying $0.01<x<1$, $0\leq y\leq 1$, $0\leq z\leq 1$, and $x+y+z=1$, respectively, and M is at least one element selected from Mn, V, Mg, Mo, Nb, Fe, Cu, and Al), and $LiFePO_4$. Among those, from the viewpoints of a battery capacity and an energy density, $Li(Ni_xCo_yM_z)O_2$ (x, y, and z are numerical values satisfying $0.1\leq x<1$, $0.1\leq y<1$, $0.1\leq z<1$, and $x+y+z=1$, respectively, and M is at least one element selected from Mn and Al) is preferable, and $Li(Ni_xCo_yAl_z)O_2$ (x, y, and z are numerical values satisfying $0.5\leq x<1$, $0.1\leq y\leq 0.4$, $0.1\leq z\leq 0.2$, and $x+y+z=1$, respectively) is more preferable.

The negative electrode active material layer 6 mainly includes a negative electrode active material. Examples of the negative electrode active material include a material capable of absorbing and releasing lithium. Examples of such a material include carbon materials such as graphite and amorphous carbon, and oxide materials such as indium oxide, silicon oxide, tin oxide, zinc oxide, lithium titanate, and lithium oxide. As the negative electrode active material, a lithium metal and a metal material capable of forming an alloy with lithium can be used. Examples of the metal capable of forming an alloy with lithium include Cu, Sn, Si, Co, Mn, Fe, Sb, and Ag, and a binary or ternary alloy including any of these metals and lithium can also be used. These negative electrode active materials may be used singly or in mixture of two or more kinds thereof.

The positive electrode active material layer 3 and the negative electrode active material layer 6 may each further contain a binder. Examples of the binder include polyvinylidene difluoride (PVdF), a vinylidene fluoride-hexafluoropropylene copolymer, a vinylidene fluoride-tetrafluoroethylene copolymer, a styrene-butadiene copolymer rubber, carboxymethyl cellulose, polytetrafluoroethylene, polypropylene, polyethylene, polyimide, polyamideimide, polyacrylic acid, polyvinyl alcohol, acrylic acid-polyacrylonitrile, polyacrylamide, polymethacrylic acid, and a copolymer thereof. The binders may be the same as or different from each other in the positive electrode active material layer and the negative electrode active material layer. The content of the binder in each of the positive electrode active material layer 3 and the negative electrode active material layer 6 may be 0.1% to 20% by mass with respect to the mass of the positive electrode active material layer 3 or the negative electrode active material layer 6.

The positive electrode active material layer 3 and the negative electrode active material layer 6 may each further include an electrically conductive auxiliary material for the purpose of reducing the resistance. Examples of the electrically conductive auxiliary material include carbonaceous fine particles and carbon fibers, such as graphite, carbon black, acetylene black, and ketjen black. The content of the electrically conductive auxiliary material in each of the positive electrode active material layer 3 and the negative electrode active material layer 6 may be 0.1% to 5% by mass with respect to the mass of the positive electrode active material layer 3 or the negative electrode active material layer 6.

As the separator 9, for example, a porous film formed of polyethylene, polypropylene, a fluorine resin, or the like can be used.

Specific forms such as the shape, the thickness, and the like of each of members constituting the electricity storage device can be appropriately set by those skilled in the art. The configurations of the electricity storage device are not limited to the embodiment of FIG. 1 and can be modified as appropriate.

EXAMPLES

1. Synthesis of Additives

Synthesis Example 1

Synthesis of 3-Methanesulfonyl Tetrahydrothiophene-1,1-Dioxide (Compound 1)

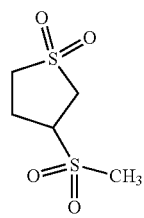

3-Sulfolene (5.9 g, 50 mmol), methyl mercaptan soda (3.5 g, 50 mmol), and 50 ml of water were added to a four-necked flask having a capacity of 200 mL, equipped with a stirrer, a condenser, a thermometer, and a dropping funnel. The reaction solution in the flask was warmed to 60° C. and then stirred for 2 hours while maintaining the same temperature. Thereafter, the reaction solution was subjected to liquid separation to obtain an oil phase. The obtained oil phase was put into to a four-necked flask having a capacity of 200 mL, equipped with a stirrer, a condenser, a thermometer, and a dropping funnel, and 100 ml of acetonitrile and potassium permanganate (39.5 g, 250 mmol) were added thereto. The reaction solution in the flask was stirred for 20 hours while maintaining the temperature at 27° C. Thereafter, solids including excess potassium permanganate and the like were removed by filtration and the filtrate was concentrated to obtain a compound 1. The yield of the compound 1 was 68% with respect to 3-sulfolene. The molecular weight of the obtained compound 1 was confirmed to be 198 by a GC/MS spectrum.

Synthesis Example 2

Synthesis of 3-Ethanesulfonyl Tetrahydrothiophene-1,1-Dioxide (Compound 2)

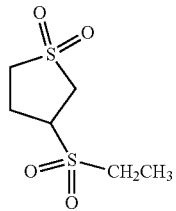

11.8 g of compound 2 was obtained by performing a reaction in the same manner as in Synthesis Example 1, except that methyl mercaptan soda was changed to ethyl mercaptan soda (4.2 g, 50 mmol). The yield of the compound 2 was 51% with respect to 3-sulfolene. The molecular weight of the obtained compound 2 was confirmed to be 212 by a LC/MS spectrum.

Synthesis Example 3

Synthesis of 3-Tert-Butylsulfonyl Tetrahydrothiophene-1,1-Dioxide (Compound 3)

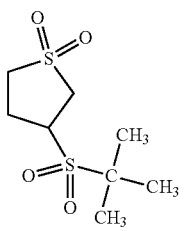

Compound 3 was obtained by carrying out a reaction in the same manner as in Synthesis Example 1, except that methyl mercaptan soda was changed to 3-tert-butylmercaptan soda (5.6 g, 50 mmol). The yield of the compound 3 was 40% with respect to 3-sulfolene. The molecular weight of the obtained compound 3 was confirmed to be 240 by a LC/MS spectrum.

Synthesis Example 4

Synthesis of 3-Acetyltetrahydrothiophene-1,1-Dioxide (Compound 4)

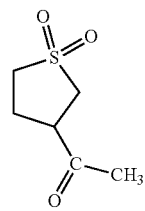

3-(1-Hydroxyethyl)tetrahydrothiophene-1,1-dioxide (3.5 g, 50 mmol), potassium permanganate (39.5 g, 250 mmol), and 100 ml of acetonitrile were added to a four-necked flask having a capacity of 200 mL, equipped with a stirrer, a condenser, a thermometer, and a dropping funnel. The reaction solution in the flask was stirred for 20 hours while maintaining the temperature at 27° C. The solids were removed by filtration and a liquid layer obtained as the filtrate was concentrated to obtain compound 4. The yield of the compound 4 was 68% with respect to 3-(1-hydroxyethyl) tetrahydrothiophene-1,1-dioxide. The molecular weight of the obtained compound 4 was confirmed to be 162 by a GC/MS spectrum.

Synthesis Example 5

Synthesis of 3-Thiophenesulfonic Acid Tetrahydroxy-1,1-dioxide (Compound 5)

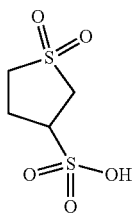

3-Bromosulfolane (9.9 g, 50 mmol), sodium sulfite (9.5 g, 75 mmol), 100 ml of acetonitrile, and 100 ml of water were added to a four-necked flask having a capacity of 200 mL, equipped with a stirrer, a condenser, a thermometer, and a dropping funnel. The reaction solution in the flask was stirred for 48 hours under the condition of reflux. The solids were removed by filtration and the filtrate was concentrated to obtain compound 5. The yield of the compound 5 was 68% with respect to 3-bromosulfolane. The molecular weight of the obtained compound 5 was confirmed to be 162 by a GC/MS spectrum.

2. Fabrication of Nonaqueous Electrolyte Solution Secondary Battery

Examples 1 to 4 and Comparative Examples 1 to 4

$Li(Ni_{0.8}Co_{0.1}Mn_{0.1})O_2$ as a positive electrode active material and carbon black as an electrical conductivity-imparting agent were dry-mixed. The obtained mixture was uniformly dispersed in N-methyl-2-pyrrolidone (NMP) in which polyvinylidene difluoride (PVDF) as a binder had been dissolved, thereby preparing a slurry. The obtained slurry was applied onto both surfaces of an aluminum metal foil (rectangular, a thickness of 20 μm). The coating film was dried to remove the NMP and the whole film was pressed to manufacture a positive electrode sheet having the aluminum metal foil as a positive electrode collector and positive electrode active material layers formed on both surfaces of the aluminum metal foil. A ratio of the solid contents in the positive electrode sheet was positive electrode active material:electrical conductivity-imparting agent:PVDF=92:5:3 in terms of a mass ratio.

Graphite powder as the negative electrode active material and carbon black as an electrical conductivity-imparting agent were dry-mixed. The obtained mixture, styrene-butadiene rubber (SBR), and carboxymethyl cellulose (CMC) were uniformly dispersed in water to prepare a slurry. The obtained slurry was applied onto one surface of a copper foil (rectangular, thickness of 10 μm). The coating film was dried to remove water and the whole film was pressed to obtain a negative electrode sheet having the copper foil as a negative electrode collector and negative electrode active material layers formed on one surface of the copper foil. A ratio of the solid contents in the negative electrode sheet was negative electrode active material:CMC:SBR=98:1:1 in terms of a mass ratio.

The negative electrode sheet fabricated above, a separator formed of polyethylene, the positive electrode sheet, a separator formed of polyethylene, and the negative electrode sheet were laminated in this order to manufacture a battery element. This battery element was put into a bag formed of a laminated film having aluminum (thickness of 40 μm) and resin layers coating both sides of the aluminum such that the terminals of the positive electrode sheet and the negative electrode sheet protruded from the bag. Subsequently, the nonaqueous electrolyte solution in each of Examples and Comparative Examples was poured into the bag. The bag was vacuum-sealed to obtain a sheet-shaped nonaqueous electrolyte solution secondary battery. Further, the sheet-shaped nonaqueous electrolyte solution secondary battery was sandwiched between glass plates and pressurized in order to increase the adhesiveness between the electrodes. The nonaqueous electrolyte solution in each of Examples and Comparative Examples was prepared by dissolving the additive and the electrolyte obtained in each of Synthesis Examples 1 to 4 in a solvent at a concentration described in Table 1. The concentration of the electrolyte was set to 1 mol with respect to 1 L of the solvent. The concentration of the additive shown in the table was set to 1% by mass with respect to the total mass of the nonaqueous electrolyte solution. A mixed solvent obtained by mixing ethylene carbonate (EC) and diethyl carbonate (DEC) at a volume ratio of EC:DEC=30:70 was used as the solvent.

Example 5 and Comparative Example 5

$Li(Ni_{0.80}Co_{0.15}Al_{0.05})O_2$ as a positive electrode active material and carbon black as an electrical conductivity-imparting agent were dry-mixed. The obtained mixture was uniformly dispersed in N-methyl-2-pyrrolidone (NMP) in which polyvinylidene difluoride (PVDF) as a binder had been dissolved, thereby preparing a slurry. The obtained slurry was applied onto both surfaces of an aluminum metal foil (rectangular, a thickness of 20 μm). The coating film was dried to remove the NMP and the whole film was pressed to obtain a positive electrode sheet having the aluminum metal foil as a positive electrode collector and positive electrode active material layers formed on both surfaces of the aluminum metal foil. A ratio of the solid contents in the positive electrode sheet was set to positive electrode active material: electrical conductivity-imparting agent:PVDF=92:5:3 in terms of a mass ratio.

A graphite powder as the negative electrode active material and carbon black as an electrical conductivity-imparting agent were dry-mixed. The obtained mixture, styrene-butadiene rubber (SBR), and carboxymethyl cellulose (CMC) were uniformly dispersed in water to prepare a slurry. The obtained slurry was applied onto one surface of a copper foil (rectangular, thickness of 10 μm). The coating film was dried to remove water and the whole film was pressed to obtain a negative electrode sheet having the copper foil as a negative electrode collector and negative electrode active material layers formed on one surface of the copper foil. A ratio of the solid contents in the negative electrode sheet was negative electrode active material:CMC:SBR=98:1:1 in terms of a mass ratio.

The negative electrode sheet fabricated above, a separator formed of polyethylene, the positive electrode sheet, a separator formed of polyethylene, and the negative electrode sheet were laminated in this order to manufacture a battery element. This battery element was put into a bag formed of a laminated film having aluminum (thickness of 40 μm) and resin layers coating both sides of the aluminum such that the terminals of the positive electrode sheet and the negative electrode sheet protruded from the bag. Subsequently, the nonaqueous electrolyte solution in each of Examples and Comparative Examples was poured into the bag. The bag was vacuum-sealed to obtain a sheet-shaped nonaqueous electrolyte solution secondary battery. Further, the sheet-shaped nonaqueous electrolyte solution secondary battery was sandwiched between glass plates and pressurized in order to increase the adhesiveness between the electrodes. The nonaqueous electrolyte solution in each of Examples and Comparative Examples was prepared by dissolving the compound 1 and the electrolyte in a solvent at a concentration described in Table 2. The concentration of the electrolyte was set to 1 mol with respect to 1 L of the solvent. The concentration of the additive shown in the table was set to 1% by mass with respect to the total mass of the nonaqueous electrolyte solution. A mixed solvent obtained by mixing ethylene carbonate (EC) and diethyl carbonate (DEC) at a volume ratio of EC:DEC=30:70 was used as the solvent.

3. Evaluation

The initial capacity, the initial resistance, the discharge capacity retention, the resistance increase ratio, and the amount of generated gas of each nonaqueous electrolyte solution secondary battery in each of Examples and Comparative Examples were measured by the following procedure. The evaluation results are shown in Tables 1 and 2.

3-1. Examples 1 to 4 and Comparative Examples 1 to 4

Measurement of Initial Capacity

Each nonaqueous electrolyte solution secondary battery was charged to 4.2 V at a current corresponding to 0.2 C at 25° C., and then kept at 45° C. for 24 hours. Thereafter, the nonaqueous electrolyte solution secondary battery was discharged to 3 V at a current corresponding to 0.2 C at 25° C. Next, each nonaqueous electrolyte solution secondary battery was subjected to three repeated cycles of an operation of charge to 4.2 V at a current corresponding to 0.2 C and subsequently discharge to 3 V at a current corresponding to 0.2 C, thereby aging the nonaqueous electrolyte solution secondary battery. After aging, the discharge capacity of the nonaqueous electrolyte solution secondary battery was measured by initial charge and discharge at 1 C, and the measured value was defined as an "initial capacity".

Measurement of Initial Resistance

After the initial charge and discharge, with regard to the nonaqueous electrolyte solution secondary battery charged with a capacity amounting to 50% of the initial capacity, an alternating current impedance at 25° C. was measured. The measured value was defined as an "initial resistance ($\Omega$)".

Evaluation of Discharge Capacity Retention and Resistance Increase Ratio

Each nonaqueous electrolyte solution secondary battery after the initial charge and discharge was subjected to a charge and discharge cycle test over 200 cycles at a charge rate of 1 C, a discharge rate of 1 C, a charge termination voltage of 4.2 V, and a discharge termination voltage of 3 V at 25° C. Thereafter, the discharge capacity of the nonaqueous electrolyte solution secondary battery by the charge and discharge at 1 C was measured, and the measured value was defined as "a discharge capacity after a 200-cycle test". Further, after the above-mentioned cycle test, with regard to the nonaqueous electrolyte solution secondary battery charged up to a capacity amounting to 50% of the capacity after the cycle, an alternating current impedance at 25° C. was measured. The measured value was defined as "a resistance ($\Omega$) after a 200-cycle test". The discharge capacity retention (%) and the resistance increase ratio in each battery are shown in Table 1. The "discharge capacity retention (%)" and the "resistance increase ratio" are values calculated by the following equations.

Discharge capacity retention (%)=(Discharge capacity after 200-cycle test/Initial capacity)×100

Resistance increase ratio=(Resistance ($\Omega$) after 200-cycle test/Initial resistance ($\Omega$))

Evaluation of Gas Generation

Separately from the batteries used in the evaluation of the initial resistance and the evaluation of the discharge capacity retention and the resistance increase ratio, a nonaqueous electrolyte solution secondary batteries having the same configuration including each of the nonaqueous electrolyte solutions of Examples 1 to 4 and Comparative Examples 1 to 4 were prepared. The battery was charged to 4.2 V at a charge rate of 0.2 C at 25° C. and then kept at 45° C. for 24 hours, thereby aging the battery. After the aging, the battery was discharged to 3 V at a discharge rate of 0.2 C at 25° C. Next, each nonaqueous electrolyte solution secondary battery was stabilized by initial charge and discharge involving three repeated cycles of an operation of charge to 4.2 V at 0.2 C and subsequently discharge to 3 V at 0.2 C.

With regard to the nonaqueous electrolyte solution secondary battery after the initial charge and discharge, the volume of the battery was measured by the Archimedes' method, and the measured value was defined as an "initial volume ($cm^3$)" of the battery. Thereafter, the battery was charged to 4.2 V at 1 C at 25° C., and subsequently left to stand at 60° C. for 168 hours. After leaving the battery to stand, the nonaqueous electrolyte solution secondary battery was cooled to 25° C. and then discharged to 3 V at 1 C. The volume of the battery after discharge was measured by the Archimedes' method and the measured value was defined as a volume ($cm^3$) after storage at a high temperature of the battery. "Amount of generated gas" in each battery is shown in Table 1. The "Amount of generated gas" is calculated by Equation:

(Amount of generated gas)=(Volume after storage at high temperature)−(Initial volume).

TABLE 1

| | Positive electrode active material | Electrolyte | Solvent | Additive | Discharge capacity retention (%) | Resistance increase ratio | Amt. of generated gas ($cm^3$) |
|---|---|---|---|---|---|---|---|
| Ex. 1 | $Li(Ni_{0.8}Co_{0.1}Mn_{0.1})O_2$ | $LiPF_6$ 1.0 mol/L | EC/DEC (30/70) % by volume | Cpd. 1 1.0% by mass | 91 | 1.4 | 0.13 |
| Ex. 2 | $Li(Ni_{0.8}Co_{0.1}Mn_{0.1})O_2$ | $LiPF_6$ 1.0 mol/L | EC/DEC (30/70) % by volume | Cpd. 2 1.0% by mass | 88 | 1.4 | 0.15 |

TABLE 1-continued

| | Positive electrode active material | Electrolyte | Solvent | Additive | Discharge capacity retention (%) | Resistance increase ratio | Amt. of generated gas (cm³) |
|---|---|---|---|---|---|---|---|
| Ex. 3 | Li(Ni$_{0.8}$Co$_{0.1}$Mn$_{0.1}$)O$_2$ | LiPF$_6$ 1.0 mol/L | EC/DEC (30/70) % by volume | Cpd. 3 1.0% by mass | 87 | 1.5 | 0.16 |
| Ex. 4 | Li(Ni$_{0.8}$Co$_{0.1}$Mn$_{0.1}$)O$_2$ | LiPF$_6$ 1.0 mol/L | EC/DEC (30/70) % by volume | Cpd. 4 1.0% by mass | 90 | 1.5 | 0.18 |
| Comp. Ex. 1 | Li(Ni$_{0.8}$Co$_{0.1}$Mn$_{0.1}$)O$_2$ | LiPF$_6$ 1.0 mol/L | EC/DEC (30/70) % by volume | None | 85 | 1.6 | 0.4 |
| Com. Ex. 2 | Li(Ni$_{0.8}$Co$_{0.1}$Mn$_{0.1}$)O$_2$ | LiPF$_6$ 1.0 mol/L | EC/DEC (30/70) % by volume | 1,3-Propanesultone 1.0% by mass | 86 | 1.3 | 0.2 |
| Comp. Ex. 3 | Li(Ni$_{0.8}$Co$_{0.1}$Mn$_{0.1}$)O$_2$ | LiPF$_6$ 1.0 mol/L | EC/DEC (30/70) % by volume | VC 1.0% by mass | 88 | 1.4 | 0.39 |
| Comp. Ex. 4 | Li(Ni$_{0.8}$Co$_{0.1}$Mn$_{0.1}$)O$_2$ | LiPF$_6$ 1.0 mol/L | EC/DEC (30/70) % by volume | FEC 1.0% by mass | 86 | 1.5 | 0.45 |

3-2. Example 5 and Comparative Example 5

The initial capacity and the initial resistance of the nonaqueous electrolyte solution secondary battery were measured by the same methods as in Examples 1 to 4 and Comparative Examples 1 to 4. The charge and discharge cycle test of the nonaqueous electrolyte solution secondary battery was performed under the same condition as in Examples 1 to 4 and Comparative Examples 1 to 4, except that the number of cycles in the charge and discharge cycle test was changed to 30, thereby measuring a resistance (Ω) after the 30-cycle test. From the obtained measured value, a discharge capacity retention was calculated by the following equation.

Discharge capacity retention (%)=(Discharge capacity after 30-cycle test/Initial capacity)×100

The discharge capacity retention (%) and the initial resistance ratio in each battery are shown in Table 2. The initial resistance ratio shown in Table 2 is a relative value of the initial resistance in a case where the initial resistance in Comparative Example 5 not using an additive was taken as 100.

TABLE 2

| | Positive electrode active material | Electrolyte | Solvent | Additive | Discharge capacity retention (%) | Initial resistance ratio |
|---|---|---|---|---|---|---|
| Ex. 5 | Li(Ni$_{0.80}$Co$_{0.15}$Al$_{0.05}$)O$_2$ | LiPF$_6$ 1.0 mol/L | EC/DEC (30/70) % by volume | Compound 1 1.0% by mass | 99.3 | 96 |
| Comp. Ex. 5 | Li(Ni$_{0.80}$Co$_{0.15}$Al$_{0.05}$)O$_2$ | LiPF$_6$ 1.0 mol/L | EC/DEC (30/70) % by volume | None | 98.7 | 100 |

From the evaluation results shown in Tables 1 and 2, it was confirmed that the charge characteristics and the resistance characteristics of the nonaqueous electrolyte solution secondary battery are improved by applying a nonaqueous electrolyte solution including an additive including the compound represented by formula (1), and generation of a gas from the nonaqueous electrolyte solution is suppressed.

REFERENCE SIGNS LIST

1: nonaqueous electrolyte solution secondary battery, 2: positive electrode collector, 3: positive electrode active material layer, 4: positive electrode plate, 5: negative electrode collector, 6: negative electrode active material layer, 7: negative electrode plate, 8: nonaqueous electrolyte solution, 9: separator

The invention claimed is:

1. An additive for a nonaqueous electrolyte solution, comprising a compound represented by the following formula (1):

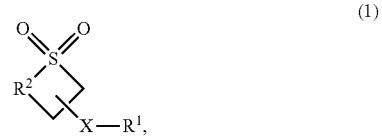

wherein in formula (1),
X represents a sulfonyl group or a carbonyl group,
when X is a sulfonyl group, R$^1$ represents an alkoxy group having 1 to 4 carbon atoms, which may be substituted with a halogen atom, an alkenyloxy group having 2 to 4 carbon atoms, which may be substituted with a halogen atom, an alkynyloxy group having 2 to 4 carbon atoms, which may be substituted with a halogen atom, an aryloxy group, which may be substituted with a halogen atom, a hydroxyl group, or a lithium oxy group, when X is a carbonyl group, $R^1$ represents an alkyl group that has 1 to 4 carbon atoms, which may be substituted with a halogen atom, an alkenyl group having 2 to 4 carbon atoms, which may be substituted with a halogen atom, an alkynyl group having 2 to 4 carbon atoms, which may be substituted with a halogen atom, an aryl group, which may be substituted with a halogen atom, an alkoxy group having 1 to 4 carbon atoms, which may be substituted with a halogen atom, an alkenyloxy group having 2 to 4 carbon atoms, which may be substituted with a halogen atom, an alkynyloxy group having 2 to 4 carbon atoms, which may be substituted with a halogen atom, an aryloxy group, which may be substituted with a halogen atom, a hydroxyl group, or a lithium oxy group, and $R^2$ represents a hydrocarbon group having 1 to 3 carbon atoms, which may be substituted with a halogen atom.

2. The additive for a nonaqueous electrolyte solution according to claim 1, wherein the compound represented by formula (1) is a compound represented by the following formula (2):

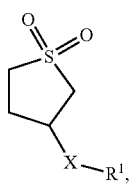

(2)

wherein in formula (2), X and $R^1$ have the same definitions as X and $R^1$, respectively, in formula (1).

3. The additive for a nonaqueous electrolyte solution according to claim 1,
wherein X is a sulfonyl group.

4. The additive for a nonaqueous electrolyte solution according to claim 1,
wherein X is a carbonyl group, and $R^1$ is an alkyl group having 1 to 4 carbon atoms, which may be substituted with a halogen atom.

5. A nonaqueous electrolyte solution comprising:
the additive for a nonaqueous electrolyte solution according to claim 1;
a nonaqueous solvent; and
an electrolyte.

6. The nonaqueous electrolyte solution according to claim 5,
wherein the nonaqueous solvent comprises a cyclic carbonate and a chained carbonate.

7. The nonaqueous electrolyte solution according to claim 5,
wherein the electrolyte is an electrolyte comprising a lithium salt.

8. An electricity storage device comprising:
the nonaqueous electrolyte solution according to claim 5;
a positive electrode; and
a negative electrode.

9. The electricity storage device according to claim 8, wherein the electricity storage device is a lithium ion battery.

10. The electricity storage device according to claim 8, wherein the electricity storage device is a lithium ion capacitor.

11. An electricity storage device comprising:
a nonaqueous electrolyte solution;
a positive electrode plate; and
a negative electrode plate,
the positive electrode plate and the negative electrode plate being arranged to face each other via the nonaqueous electrode solution,
wherein the nonaqueous solution comprises a compound represented by the following formula (1):

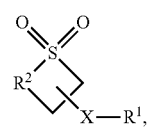

(1)

wherein in formula (1),
X represents a sulfonyl group or a carbonyl group,
when X is a sulfonyl group, $R^1$ represents a methyl group, an ethyl group, an n-propyl group, an isopropyl group, an n-butyl group, an isobutyl group, a t-butyl group, or a hydroxyl group,
when X is a carbonyl group, R1 represents an alkyl group that has 1 to 4 carbon atoms, which may be substituted with a halogen atom, an alkenyl group having 2 to 4 carbon atoms, which may be substituted with a halogen atom, an alkynyl group having 2 to 4 carbon atoms, which may be substituted with a halogen atom, an aryl group which may be substituted with a halogen atom, an alkoxy group having 1 to 4 carbon atoms, which may be substituted with a halogen atom, an alkenyloxy group having 2 to 4 carbon atoms, which may be substituted with a halogen atom, an alkynyloxy group having 2 to 4 carbon atoms, which may be substituted with a halogen atom, an aryloxy group which may be substituted with a halogen atom, a hydroxyl group, or a lithium oxy group, and $R^2$ represents a hydrocarbon group having 1 to 3 carbon atoms, which may be substituted with a halogen atom,
the positive electrode plate comprises a positive electrode collector, and a positive electrode active material layer provided on the inner surface side of the positive electrode collector, and
the positive electrode active material layer comprises:
$Li(Ni_xCo_yAl_z)O_2$, wherein x, y, and z are numerical values satisfying 0.5≤x<1, 0.1≤y≤0.4, 0.1≤z≤0.2, and x+y+z=1; or
$Li(Ni_xCo_yM_z)O_2$, wherein x, y, and z are numerical values satisfying 0.1≤x<1, 0.1≤y<1, 0.1≤z<1, and x+y+z=1, and M is Mn.

12. An electricity storage device according to claim 11, wherein in formula (1),
X is a sulfonyl group,
$R^1$ is a methyl group, and
the positive electrode active material layer comprises $Li(Ni_xCo_yAl_z)O_2$, wherein x, y, and z are numerical values satisfying 0.5≤x<1, 0.1≤y≤0.4, 0.1≤z≤0.2, and x+y+z=1.

13. An electricity storage device according to claim 11, wherein in formula (1), X is a sulfonyl group,
R¹ is a methyl group, and
the positive electrode active material layer comprises
  Li(Ni$_x$Co$_y$M$_z$)O$_2$, wherein x, y, and z are numerical values satisfying $0.1 \leq x < 1$, $0.1 \leq y < 1$, $0.1 \leq z < 1$, and $x+y+z=1$, and M is Mn.

* * * * *